United States Patent
Hotta et al.

[11] Patent Number: 4,626,337
[45] Date of Patent: Dec. 2, 1986

[54] OXYGEN SENSOR

[75] Inventors: Yasumichi Hotta, Mie; Takao Akatsuka, Aichi; Masao Kawaguchi, Toyota; Jiro Nakano, Okazaki; Takao Ishibashi, Toyota, all of Japan

[73] Assignees: Nippondenso Co., Ltd., Kariya; Toyota Jidosha Kabushiki Kaisha, Toyota, both of Japan

[21] Appl. No.: 729,854

[22] Filed: May 2, 1985

[30] Foreign Application Priority Data

May 7, 1984 [JP] Japan .............................. 59-66875[U]

[51] Int. Cl.⁴ ............................................ G01N 27/46
[52] U.S. Cl. ..................................... 204/429; 204/427
[58] Field of Search ......................... 204/1 S, 421–429

[56] References Cited
U.S. PATENT DOCUMENTS 4,121,988 10/1978 Sano et al. .
4,476,008 10/1984 Sano et al. ........................... 204/425

FOREIGN PATENT DOCUMENTS 58-100746  6/1983  Japan .

Primary Examiner—T. Tung
Attorney, Agent, or Firm—Cushman, Darby & Cushman

[57] ABSTRACT

The oxygen sensor has a solid electrolytic element made of an oxygen ion-conducting metal oxide. This element is formed in a cup shape, closed at one end and opened at its other end. The outer peripheral surface of the element is exposed to exhaust gas, and the inner peripheral surface of the element is exposed to the atmosphere. A first electrode is fixed to the outer peripheral surface of the element, and a second electrode is fixed to the inner peripheral surface of the element. An electrically insulating layer is formed on the outer peripheral surface of the element except where the first electrode is disposed. A metal lead of thin film, connected to the first electrode, is formed on the insulating layer. Further, a retaining lead connected to the first electrode is formed on the metal lead. This retaining lead is formed by densely sintering a conductive material and a binding material.

5 Claims, 6 Drawing Figures

FIG. 1
FIG. 2
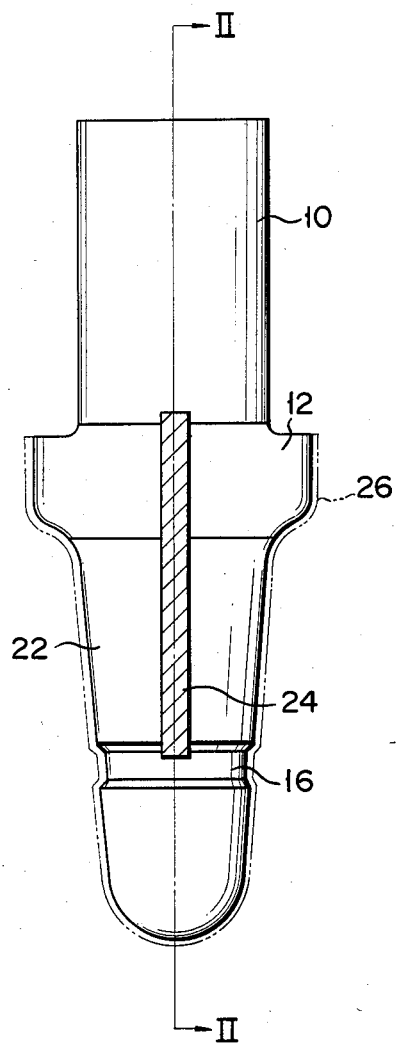
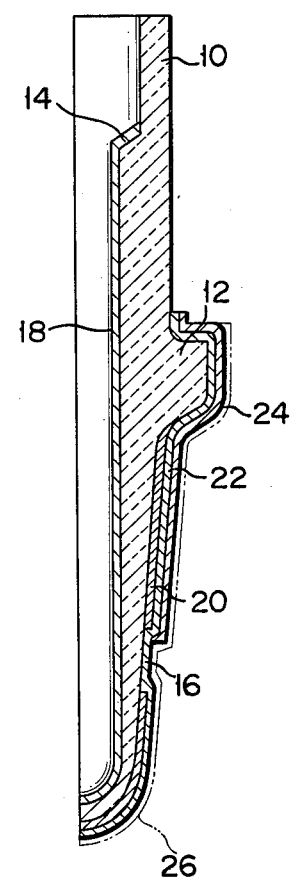

4,626,337

OXYGEN SENSOR

BACKGROUND OF THE INVENTION

The present invention relates to an oxygen sensor for detecting the concentration of oxygen contained in a subject gas, and more particularly to an oxygen sensor used to control an air-fuel ratio of a mixture air in an internal combustion engine by detecting the concentration of oxygen in exhaust gas of the engine.

An oxygen sensor of this type is disclosed, for example, in U.S. Pat. No. 4,121,988 and Japanese Patent Disclosure No. 100746/83. The conventional oxygen sensor has a solid electrolytic element made of an oxygen ion conducting metal oxide. The element has a first surface exposed to exhaust gas of an internal combustion engine and a second surface exposed to atmospheric air as a reference gas. First and second electrodes are respectively fixed to the first and second surfaces of the element. An electrically insulating layer made of a heat resistant ceramic material is formed on the first surface of the element except that portion to which the first electrode is fixed. Lead of thin film electrically connected to the first electrode is further formed on the insulating layer. Additionally, a gas diffusion resisting layer made of a porous electrically insulating ceramic material is formed on the first electrode, the insulating layer and the lead.

When a predetermined voltage is applied between the first electrode and the second electrode of this oxygen sensor, a current proportional to the concentration of oxygen in the exhaust gas flows between the first electrode and the second electrode, and the concentration of oxygen in the exhaust gas can be detected by measuring the current.

However, although the lead of the oxygen sensor is covered with a resisting layer, the lead is exposed to the exhaust gas (which largely varies in temperature) through the resisting layer. Further, since the resisting layer covered on the lead is porous and the outer surface of the insulating layer formed on the lead is rough, metallic particles of the lead of the thin film are apt to cohere when the oxygen sensor is used for a long period of time. Thus, it is a drawback that the lead of the oxygen sensor is locally disconnected at some positions. Therefore, the electric resistance of the lead increases. The lead is completely disconnected in the worst case. As a result, it is impossible to detect the concentration of oxygen.

SUMMARY OF THE INVENTION

It is an object of the present invention to provide a durable oxygen sensor which can accurately detect the concentration of oxygen even if the sensor used for a long period of time.

In order to achieve the above and other objects, there is provided according to the present invention an oxygen sensor comprising:

a solid electrolytic element made of an oxygen ion conducting metal oxide having a first surface exposed to a subject gas to be detected and a second surface exposed with a reference gas;

a porous first electrode fixed onto the first surface of the element;

a porous second electrode fixed onto the second surface of the element;

an electrically insulating layer made of a heat resisting ceramic material formed on the first surface of the element except the position to which the first electrode is fixed;

metal lead of film formed on the insulating layer and electrically connected to the first electrode;

a retaining element formed on the metal lead and connected to the first electrode, and formed by densely sintering a conducting metal material and a binding material on the metal lead; and a gas diffusion resisting layer made of a porous electrically insulating ceramic for covering the first electrode, the metal lead and the retaining element.

According to the oxygen sensor of the present invention, the retaining element is formed of a sintered member formed by densely sintering the conducting metal material and the binding material. Therefore, one surface of the metal lead is preferably in contact with the retaining element. Thus, even if the metal particles of the lead cohere on one surface, the cohesion is limited by the retaining element. In addition, when the retaining element is made of the sintered material, the binding material of the retaining element is also rigidly coupled to the metal particles of the lead. Therefore, cohesion of the metal particles of the lead can be preferably prevented. Consequently, even if the oxygen sensor is used for a long period of time, the metal lead can reliably maintain its function, thereby improving the durability of the oxygen sensor.

Even if the metal particles of the lead cohere on the other side surface, to which the insulating layer is connected, thereby resulting in the disconnection of the lead, the retaining element performs a function as the lead to the first electrode because the retaining element has a conductivity, thereby reliably maintaining the durability of the oxygen sensor.

BRIEF DESCRIPTION OF THE DRAWINGS

FIG. 1 is a side view of an oxygen sensor of a first embodiment according to the present invention;

FIG. 2 is a partial longitudinal sectional view of the oxygen sensor along the line II—II of FIG. 1;

DETAILED DESCRIPTION OF THE PREFERRED EMBODIMENTS

Figure 3:
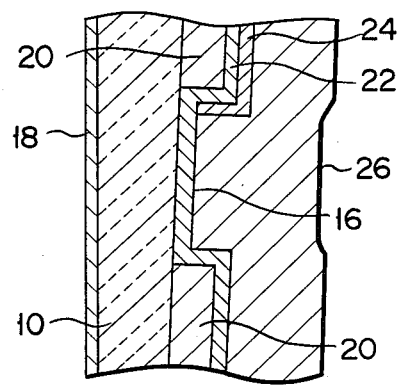
FIG. 3 is a fragmentary sectional view on an enlarged scale, showing a respective portion of the oxygen sensor of FIGS. 1 and 2.

Referring to FIGS. 1 to 3, the fundamental construction of an oxygen sensor of a first embodiment according to the present invention is shown. An oxygen sensor has a solid electrolytic element 10. The element 10 is opened at one end, and is formed in a cup shape closed at the other end. When the element 10 is exposed, for example, on the outer surface to a subject gas to be detected and exposed on the inner surface to a reference gas such as atmospheric air, the element 10 generates an electromotive force responsive to the concentration of oxygen in the subject gas between the outer surface and the inner surface. Further, as the element 10 is formed of an oxygen ion-conducting metal oxide having a characteristic that its electric resistance decreases as the element is heated. For instance, the metal oxide is a dense, sintered material produced by the solid solution of 95 mol % of $ZrO_2$ and 5 mol % of $Y_2O_3$. A flange 12 is integrally formed at the center portion of the outer peripheral surface of the element 10. On the other hand, an annular stepped portion 14 is formed, as shown in FIG. 2, on the inner peripheral surface of the element 10 at the side of the open end.

A first electrode 16 made of a thin, porous film of platinum Pt is fixed to a part of the outer peripheral surface of the element 10 at the closed end side. The area of the first electrode 16 is 20 $mm^2$ to 100 $mm^2$. The thickness of the element 10, to which the first electrode 16 is fixed, is 0.1 mm to 0.8 mm. On the other hand, a second electrode 18 also made of a thin, porous film of platinum Pt is fixed to the inner peripheral surface of the element 10. The second electrode 18 is formed, as shown in FIG. 2, on the entire inner surface which extends from the stepped portion 14 of the element 10 to the inner surface of the closed end. It is noted that the first and second electrodes 16 and 18 are not limited to the particular platinum, but may be made of a material having a catalytic action such as Pd or an alloy material.

In FIGS. 1 and 2, an electrically insulating layer 20 made of a heat resisting ceramic material is covered on the outer peripheral surface of the element 10 below the flange 12, except the portion to which the first electrode 16 is fixed. A thin metal lead 22, electrically connected to the first electrode 16, is formed on the insulating layer 20. The lead 22 extends over the flange 20, and is formed on the outer peripheral surface of the element 10.

The sequence of forming the first electrode 16, the insulating layer 20 and the lead 22 on the outer peripheral surface of the element 10 will now be described. A mask member is first covered at the position on the outer peripheral surface of the element 10, to which the first electrode 16 is fixed. Then, a heat resistance insulating ceramic material such as alumina or alumina-magnesia spinel is covered by plasma spraying on the outer peripheral surface of the element 10 to form an electrically insulating layer 20. The insulating layer 20 has a thickness of approximately 100 micron. After the insulating layer 20 is completely coated, the mask member is removed from the element 10, and platinum is coated by chemical plating on the outer peripheral surface of the element 10 and the insulating layer 20. Thus, as best shown in FIG. 3, the first electrode 16 is formed on the outer peripheral surface of the element 10 covered with the mask member, and the metal lead 22 is formed simultaneously with the formation of the first electrode 16. Therefore, the lead 22 is covered on the entire surface of the insulating layer 20.

As shown by hatched lines in FIG. 1, at least one retaining lead 24 is formed on the metal lead layer 22. The retaining lead 24 is electrically connected at one end to the first electrode 16, extends axially of the element 10, and at its other end to the position slightly above the upper end of the lead 22 in FIG. 1. The sequence of forming the retaining lead 24 will now be described in detail. A material of paste state formed by adding and mixing an organic solvent with a mixture which contains, for example, 80 vol. % of platinum powder (having 2 micron of particle size) and 20 vol. % of borosilicate glass powder, is coated by brushing, by using a transfer press which has an electric transfer body, or by a dispenser. Then, the entire element 10, on which the metal lead layer 22 and the retaining lead 24 are formed, is heated to 1000° to 1100° C. to sinter the lead layer 22 and the lead 24. The borosilicate glass and the platinum particles of the components of the lead 24 are not only rigidly coupled by sintering, but the borosilicate glass of the lead 24 is also rigidly coupled to the platinum particles of the lead 22. More specifically, the lead layer 22 and the lead 24 are coupled rigidly to each other. The thickness of the lead 24 thus formed is 5 micron. In the embodiment of the invention, a powder of metal oxide having electric insulation such as zirconia or alumina may be used instead of the borosilicate glass of the component of the lead 24. Further, the retaining lead 24 contains preferably 55 to 95 vol. % of the conducting metal material and 45 to 5 vol. % of the binding material, and the lead 24 is not limited to one, but may be constituted by two or more similar such leads.

Further, the first electrode 16, the metal lead layer 22 and the lead 24 are covered with a gas diffusion-resisting layer 26. The resisting layer 26 is formed by plasma spraying a ceramic material having porous electric insulation such as $Al_2O_3$ or $ZrO_2$ to the outer surfaces of the first electrode 16, the lead layer 22 and the lead 24. In the embodiment, the layer 26 is formed by plasma spraying. However, the invention is not limited to the particular embodiment. For example, the layer 26 may be formed by bonding a preformed ceramic filter. In FIGS. 1 and 2, the layer 26 is designated by a two-dotted chain line.

Figure 5:
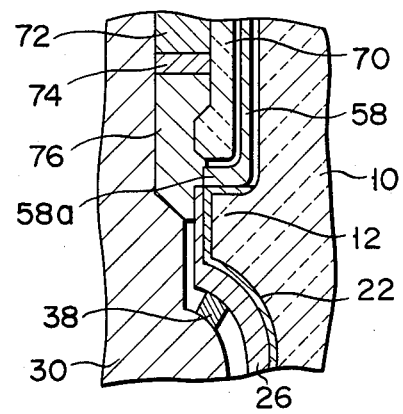
FIG. 5 is an enlarged view of the portion V in FIG. 4.
Figure 6:
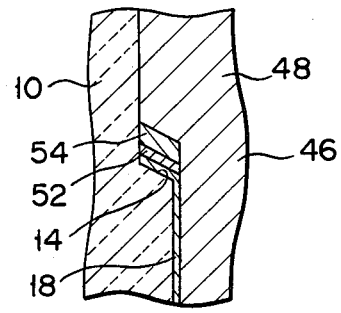
FIG. 6 is an enlarged view of the portion IV in FIG. 4.
Figure 4:
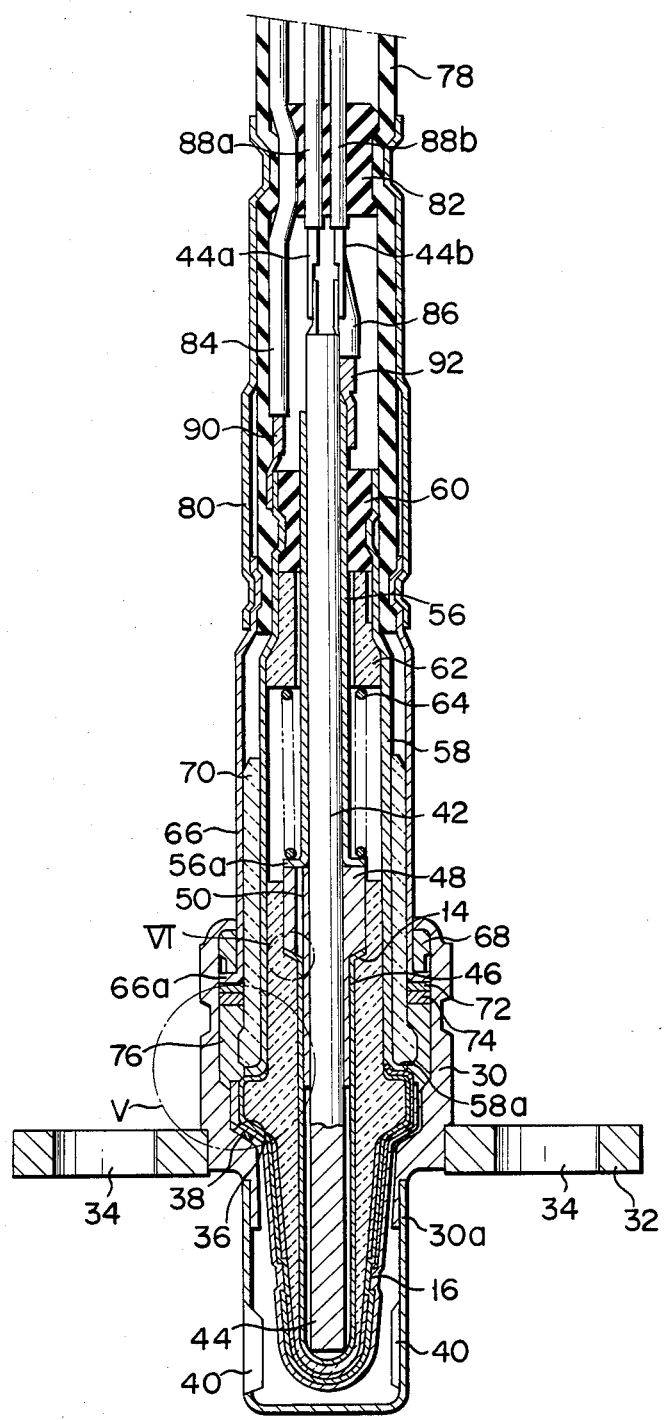
FIG. 4 is a longitudinal sectional view of an assembly of apparatus illustrating the oxygen sensor of FIGS. 1–3 in use.

Examples of use of the oxygen sensor of the invention will now be described with reference to FIGS. 4 to 6.

The oxygen sensor is hold fixedly into a cylindrical metal housing 30. A mounting flange 32 is fixed to the outer peripheral surface of the housing 30. A plurality of bolt inserting holes 34 are formed at the flange 32. Therefore, the housing 30 can be mounted on an exhaust manifold of an engine through the flange 32 and bolts inserted into the holes 34.

An annular sheet 36 is formed on the inner peripheral surface of the housing 30. Therefore, the flange 12 of the oxygen sensor is rested, as shown in FIG. 5, on an annular sheet 36 through a ring packing 38. When the oxygen sensor is mounted in the housing 30 as described above, the lower side of the oxygen sensor is projected from the housing 30 as shown. Thus, the oxygen sensor can be exposed to the exhaust gas flowing in the exhaust manifold. A protecting cover 30a for covering the position of the oxygen sensor projected into the exhaust manifold is mounted in the housing 30, and a plurality of holes 40 for introducing the exhaust gas into the interior are formed at the cover 30a.

A ceramic heater 42 of a rod shape is inserted into the oxygen sensor. The heater 42 contains a heating wire 44 with a coiled or pectinated shape made, for example, of a nichrome wire in a ceramic body made of an alumina. A metal pipe 46 is disposed between the outer peripheral surface of the ceramic heater 42 and the inner peripheral surface of the oxygen sensor. In the drawings, a flange 48 is formed at the upper end of the pipe 46, and at least one or more of through-holes 50 which extend axially are formed at the flange 48. The pipe 46 is bonded to the outer peripheral surface of the heater 42 by, for example, silver brazing. The pipe 46 is held, as best seen in FIG. 6, in such a manner that the flange 48 is contacted with the stepped portion 14 of the element 10 through a ring packing 52 made of Cu and a graphite ring 54 compression molded. Therefore, the pipe 44 and the second electrode 18 of the oxygen sensor are electrically connected through the packing 52 and the ring 54.

The ceramic heater 42 projected from the pipe 46 is covered with a metal pipe 56. A flange 56a is formed on one end of the pipe 56, and contacted with the upper end of the pipe 48. Further, a metal pipe 58 is disposed concentrically at the outside of the pipe 56. In the drawings, the open end of the element 10 is shown inserted into the lower end of the pipe 58, and a flange 58a formed at the lower end of the pipe 58 is electrically connected to the leads 22 and 24 extending over the flange 12 of the element 10. On the other hand, a ring 60 made of silicone rubber is fitted into the upper end of the pipe 58, and the ring 60 is secured by caulking (i.e. squeeze-forming, e.g., crimping) the pipe 58.

An insulating element 62 with a ring shape formed of alumina is disposed at the lower side from the ring 60. A coiled spring 64 is disposed between the insulating element 62 and the flange 56a of the pipe 56, and the pipe 46 is pressed by the spring 64 through the flange 56a of the pipe 56.

A protecting pipe 66 is disposed concentrically with the pipe 58 at the outside of the pipe 58. In the drawings, the lower end of the pipe 66 is engaged within the housing 30, and a flange 66a is formed at the lower end of the pipe 66. A metal ring 68 is disposed between the inner end of the top side of the housing 30 and the flange 66a of the pipe 66. The pipe 66 is fixed through the ring 68 by crimping the upper end of the housing 30. A cylindrical insulating element 70 made of alumina is disposed between the pipe 66 and the pipe 58. In the drawings, the upper end of the insulating element 70 extends upwardly over the upper end of the oxygen sensor, and the lower end extends to the flange 58a of the pipe 58. Further, a metal ring 72 having heat resistance, a ring 74 made of asbestos and a ring talc 76 compression molded are sequentially disposed (in the order, from the top) between the inner peripheral surface of the housing 30 and the outer peripheral surface of the insulating element 70.

In the drawings, a rubber tube 78 is shown connected to enclose the upper end of the pipe 58. Further, the lower end of the tube 78 is fitted into the upper end of the pipe 66, and a connecting pipe 80 is disposed to enclose the upper end of the pipe 66 and the lower end of the tube 78. The upper end of the pipe 66, the lower end of the tube 78 and the pipe 58 are coupled to each other by caulking (i.e. squeeze-forming) the lower end of the tube 80. On the other hand, the pipe 80 and the tube 78 are coupled to each other through a rubber bushing 82 fitted in the tube 78 by caulking (i.e. squeeze-forming) the upper end of the pipe 80.

Lead wires 84, 86, 88a, 88b which are shown extending downwardly in the drawings are disposed through the bushing 82 in the tube 78. The lower end of the lead wire 84 is welded through a terminal 90 to the upper end of the pipe 58. The lead wire 86 is welded through a terminal 92 to the pipe 56. The lead wires 88a and 88b are respectively electrically connected through terminals 44a and 44b to both ends of the heater wire 44 of the heater 42.

As described above, the first electrode 16 is connected to the lead wire 84 through the leads 22 and 24 and the pipe 58, while the second electrode 18 is connected to the lead wire 86 through the pipe 56.

The operating mode of the oxygen sensor will now be described.

The lead wire 86 is connected to the cathode of a power source (not shown), while the lead 84 is connected to the anode of the power source. More particularly, a predetermined voltage is supplied between the first electrode 16 and the second electrode 18. In this state, oxygen molecules in the exhaust gas fed through the resisting layer 26 to the first electrode 16 become oxygen ions in such a manner that electrons are supplied thereto from the first electrode 16. The oxygen ions are diffused in the element 10 to reach the second electrode 18, and, when the second electrode 18 receives electrons, the oxygen ions again become oxygen molecules. As a result, a current flows between the first electrode 16 and the second electrode 18. The oxygen molecules produced in the electrode 18 are discharged through the holes 50 of the pipe 46, from the gaps of the components, into the atmosphere.

In the diffusion process of the oxygen ions thus diffused in the element 10, the thickness of the resisting layer 26 is formed to a predetermined value or thickness such as, for example, 300 microns or thicker, and the area of the first electrode 16 is formed constantly within a range of 20 to 100 mm$^2$. In this state, if a voltage applied between the first electrode 16 and the second electrode 18 is gradually raised, the current flowing between the electrode 16 and the electrode 18 also increases. However, when the voltage increases so much as to become higher than the predetermined voltage, there arises a region where no variation occurs in the value of the current flowed between the electrode 16 and the electrode 18 by the influence of the resisting layer 26 even if the voltage is raised more than this value. In other words, under such conditions a saturated current flows between the electrode 16 and the electrode 18. This saturated current can be expressed by the following formula:

$$Il \cong (4F \times DO_2/R \times T) \times (S/L) \times PO_2$$

Here
F: Faraday constant,
R: gas constant,
DO$_2$: diffusion constant of oxygen molecules,
T: absolute temperature of element,
S: area of first electrode,
L: effective diffusion length of gas-diffusible resistance layer,
PO$_2$: partial oxygen pressure.

As apparent from the above formula, when the temperature of the element 10 is maintained constantly by the heater 42, the value of the saturated current Il varies only with the concentration of the oxygen, i.e., the partial pressure of the oxygen in the exhaust gas. Therefore, when a voltage of the predetermined value or higher, capable of generating the saturated current is applied between the first electrode 16 and the second electrode 18, the concentration of the oxygen in the exhaust gas can be detected by measuring the saturated current flowing between the electrode 16 and the electrode 18.

In the embodiments described above, the concentration of the oxygen in the exhaust gas is detected by using the oxygen sensor. However, the present invention is not limited to the particular embodiments. For example, a theoretical air-fuel ratio in the mixture gas of the engine may be detected by measuring the electromotive force generated between the first electrode and the second electrode by the difference of the concentrations of the oxygens between the exhaust gas and the atmosphere.

Further, the oxygen sensor of the invention may be used not only for detecting the concentration of the oxygen contained in the exhaust gas of the engine, but also for controlling the supply of the air, for example, in a combustion system of an blast furnace.

What is claimed is:

1. An oxygen sensor for detecting the concentration of oxygen contained in a subject gas comprising:
    a solid electrolytic element made of an oxygen ion-conducting metal oxide having a first surface adapted to be exposed to the subject gas and a second surface adapted to be exposed to a reference gas;
    a porous first electrode fixed on said first surface of said element;
    a porous second electrode fixed on said second surface of said element;
    an electrically-insulating layer made of a heat-resisting ceramic material formed on said first surface of said element except where said first electrode is fixed on said first surface;
    a metal lead formed on said insulating layer, this metal lead being made of film material and being electrically connected to said first electrode;
    an electrically-conductive retaining element formed on said metal lead, this retaining element being electrically connected to said first electrode and constituted by a densely sintered mixture of a conducting metal material and a binding material; and
    a gas diffusion-resisting layer made of a porous, electrically-insulating ceramic material, this layer covering said first electrode, said metal lead and said retaining element, this oxygen sensor thereby being adapted such that at least within a predetermined range of oxygen concentration, if said first electrode is electrically connected via said metal lead to an anode of a source of electrical power, and said second electrode is electrically connected to a cathode of said source of electrical power and a voltage applied across said electrodes thereby while said first surface is exposed to said subject gas and said second surface is exposed to said reference gas, a current will flow between said electrodes, which current is proportional to the difference between the concentration of oxygen in said subject gas and said reference gas.

2. An oxygen sensor according to claim 1, wherein the metal material of the retaining element is platinum, and the binding material of the retaining element is one selected from a group consisting of glass, zirconia and alumina.

3. An oxygen sensor according to claim 2, wherein the retaining element is formed of a composition containing 55 to 95 vol. % of platinum and 45 to 5 vol. % of glass.

4. An oxygen sensor according to claim 1, wherein the retaining element comprises at least a retaining sheet of slender shape formed on the metal lead.

5. An oxygen sensor according to claim 1, wherein the sensor further comprises a heater for heating the solid electrolyte element.

* * * * *